(12) United States Patent
Corteling et al.

(10) Patent No.: US 9,629,879 B2
(45) Date of Patent: Apr. 25, 2017

(54) THERAPEUTIC USE OF NEURAL STEM CELLS

(75) Inventors: Randolph Corteling, Guildford (GB); Caroline Hicks, Guildford (GB); John Sinden, Guildford (GB); Jack Price, London (GB)

(73) Assignee: RENEURON LIMITED (GB)

(*) Notice: Subject to any disclaimer, the term of this patent is extended or adjusted under 35 U.S.C. 154(b) by 83 days.

(21) Appl. No.: 13/701,932

(22) PCT Filed: Jul. 11, 2011

(86) PCT No.: PCT/GB2011/051289
§ 371 (c)(1),
(2), (4) Date: Mar. 13, 2013

(87) PCT Pub. No.: WO2012/004611
PCT Pub. Date: Jan. 12, 2012

(65) Prior Publication Data
US 2013/0171177 A1 Jul. 4, 2013

(30) Foreign Application Priority Data
Jul. 9, 2010 (GB) .................................. 1011589.7

(51) Int. Cl.
A61K 35/30 (2015.01)
C12N 5/0797 (2010.01)
A61K 35/12 (2015.01)

(52) U.S. Cl.
CPC ............ *A61K 35/30* (2013.01); *C12N 5/0623* (2013.01); *A61K 2035/122* (2013.01)

(58) Field of Classification Search
None
See application file for complete search history.

(56) References Cited

U.S. PATENT DOCUMENTS

2008/0219955 A1* 9/2008 Sekula ................ C12N 5/0618
424/93.7
2008/0279814 A1* 11/2008 Schaebitz ............ A61K 38/193
424/85.2

FOREIGN PATENT DOCUMENTS

EP      1 645 626 A1    4/2006
WO      WO 97/10329  *   3/1997

OTHER PUBLICATIONS

Huang et al (Surgical Neurology 66: 232-245, 2006).*
Paykel et al (Dialogues Clin Neurosci 10: 279-289, 2008).*
Jansen et al. Stem Cells Dev 19: 481-490, 2010.*
Misuzawa H (Clin Neurology 43: 832-833, 2003—abstract).*
Hodges et al. (Cell Transplant. 16: 101-115, 2007).*
Eller et al., "Pro-inflammatory cytokines and treatment response to escitaloprsam in major depressive disorder," *Progress in Neuro-Psychopharmacology & Biological Psychiatry*, Feb. 2, 2008, vol. 32 (2): 445-450.
Kempermann G et al., "Depressed New Neurons?—Adult Hippocampal Neurogenesis and a Cellular Plasticity Hypothesis of Major Depression," *Biological Psychiatry*, Sep. 1, 2003, vol. 54 (5): 499-503.
Kim Y K et al., "Cytokine imbalance in the Pathophysiology of Major Depressive Disorder," *Progress in Neuro-Psychopharmacology & Biological Psychiatry*, Jun. 30, 2007, vol. 31 (5): 1044-1053.
McAfoose J et al., "Evidence for a Cytokine Model of Cognitive Function," *Neuroscience and Behavioral Reviews*, Mar. 1, 2009, vol. 33 (3): 355-366.
Ono T et al., "The role of neural stem cells for in vitro Models of Schizophrenia: Neuroprotection via Akt/ERK signal regulation," *Schizophrenia Research*, Sep. 1, 2010, vol. 122 (1-3): 239-247.
Park D H et al., "Increased Neuronal Proliferation in the Dentate Gyrus of Aged Rats Following Neural Stern Cell Implantation," *Stem Cells and Development*, 2010, vol. 19 (2) 175-180, 177-179.
Pollock K et al., "A conditionally immortal clonal stem cell line from human cortical Neuroepithelium for the treatment of ischemic stroke," *Experimental Neurology*, May 1, 2006, vol. 199 (1): 143-155.
Stroemer Paul et al., "The Neural Stem Cell line CTX0E03 Promotes Behavioral Recovery and Endogenous Neurogenesis After Experimental Stroke in a Dose-Dependent Fashion," *Neurorehabilitation and Neural Repair*, Nov. 1, 2009, vol. 23 (9): 895-909.
Tfilin M et al.,"Mesenchymal stem cells increase Hippocampal Neurogenesis and counteract depressive-like behavior," *Molecular Psychiatry*, Dec. 1, 2010, vol. 15 (12): 1164-1175.
Thomas R J et al., "Automated, serum-free production of CTX0E03: a therapeutic clinical grade human neural stem cell line," *Biotechnology Letters*, Apr. 3, 2009, vol. 31 (8): 1167-1172.

* cited by examiner

*Primary Examiner* — Daniel E Kolker
*Assistant Examiner* — Aditi Dutt
(74) *Attorney, Agent, or Firm* — Saliwanchik, Lloyd & Eisenschenk

(57) ABSTRACT

The present invention provides an isolated cell obtainable from the CTX0E03 neural stem cell line for use in the treatment of a disorder associated with elevated levels of pro-inflammatory cytokines, wherein the disorder is selected from unipolar and bipolar depression, schizophrenia, obsessive compulsive disorder, autism and autistic syndrome disorders.

3 Claims, 10 Drawing Sheets

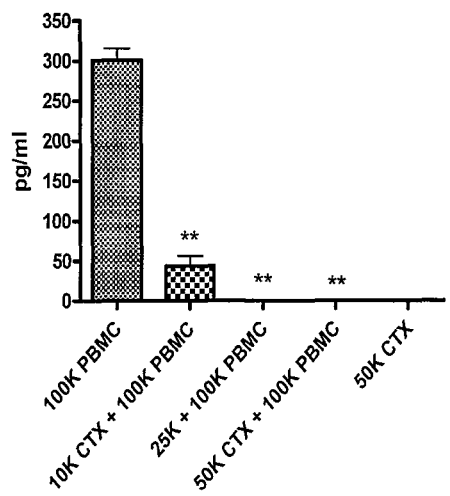 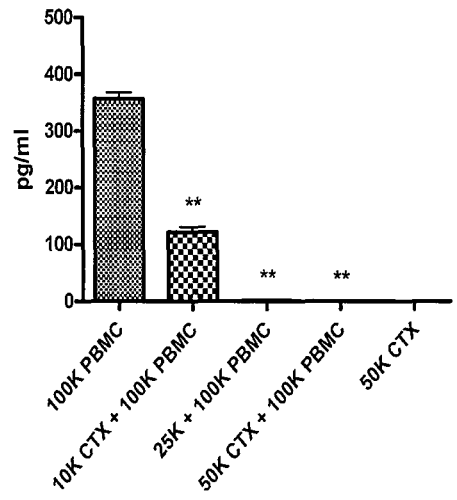
Figure 4A    Figure 4B
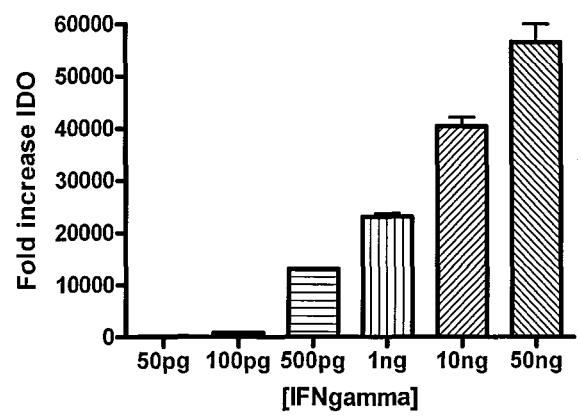
Figure 5

THERAPEUTIC USE OF NEURAL STEM CELLS

CROSS REFERENCE TO A RELATED APPLICATION

This application is a National Stage Application of International Application Number PCT/GB2011/051289, filed Jul. 11, 2011; which claims priority to Great Britain Application No. 1011589.7, filed Jul. 9, 2010; which are incorporated herein by reference in their entirety.

FIELD OF THE INVENTION

The present invention relates to the use of neural stem cells in the treatment of psychiatric disorders.

BACKGROUND TO THE INVENTION

Depression is a debilitating disorder that affects millions of people worldwide (Lopez A D and Murray C, 1998) and imposes a significant cost upon society (Gumnick and Nemeroff, 2000). It is a common psychiatric disorder with a lifetime prevalence of 10-20% (Wong and Lucinio, 2001). Recurrent symptoms are common, with more than 50% of patients experiencing more than one depressive episode. Depression is widespread in patients with co-existing illness, such as diabetes, cancer and stroke, and is particularly prevalent after experiencing heart attack. There are multiple symptoms of depression, including mood alteration, loss of appetite and fatigue; often the sufferer's day to day life is disrupted by lack of concentration, disturbed sleep and feelings of worthlessness. In the most severe cases, patients experience psychotic symptoms such as hallucinations, delusions, morbid and even suicidal thoughts.

Stress has been implicated as a key factor in the pathophysiology of depression and related psychiatric disorders (Caspi et al., 2003). Abnormalities in the hypothalamic pituitary adrenal (HPA) axis stress response (Heuser, 1998) and the reduced ability of the hippocampus to inhibit the HPA axis has been demonstrated in depressed patients (Heuser, 1998; Young et al., 1991). Structural changes of the hippocampus show a decrease in hippocampal volume in patients with depression and also those suffering from post-traumatic stress disorder (Sheline et al., 1996; Sapolsky, 1996; Bremner et al., 1995). Likewise, chronic stress (for example, restraint or systemic administration of glucocorticoids) results in atrophy of the vulnerable neurones in the hippocampus in rats and non-human primates (Watanabe et al., 1982; Saplosky et al., 1985; Uno et al., 1989; Sapolsky et al., 1990; Wooley et al., 1990; Stein-Behrens et al., 1994; Mararinos et al., 1996). These and other studies confirm that stress induced brain atrophy, loss of neurons and reduced neurogenesis in the hippocampus, may contribute to the pathophysiology of depression (Watanbe et al., 1982; Sapolsky et al., 1985; Uno et al., 1989; Wooley et al., 1990; Stein-Behrens et al., 1994; Elkis et al., 1995; Magarinos et al., 1996).

More recently, the role of pro-inflammatory cytokines in the pathopysiology of depression and related psychiatric disorders has been described. Pro-inflammatory cytokines have been shown to activate the HPA axis and innate immune system in depressed patients (Schiepers et al., 2005). Additionally patients with immune disorders have been shown to exhibit a higher incidence of depression (Dunn et al., 2005). Changes in cytokine profiles have also been demonstrated in depressed patients (Kim et al., 2007; Brambilla et al., 2004). In a clinical study, plasma taken from obsessive compulsive disorder (OCD) patients demonstrated higher levels of the pro-inflammatory cytokines tumor necrosis actor-alpha (TNFα) and interleukin-6 (IL-6) compared with healthy control patients (Konuk et al., 2007). Likewise, rodent models of depression also demonstrate elevation of pro-inflammatory cytokines. In particular, Interleukin-1 (IL-1) has been identified as a key mediator in stress induced depression in these models (Goshen et al., 2008; Koo and Duman., 2007). Evidence that IL-1 exerts an anti-neurogenic effect in these models provides further evidence to support the role of the inflammatory response in psychiatric disorders (Ben Menachem-Zidon et al., 2008).

Chronic anti-depressant treatment with selective serotonin re-uptake inhibitor drugs (SSRIs) has been reported to increase cell proliferation, granule cell survival and to reverse the detrimental effect of stress on hippocampal neurogenesis (Malberg et al., 2000; Malberg and Duman, 2003).

Current therapies for the treatment of psychiatric disorders such as depression and OCD, although efficacious in some patients, require long term, chronic treatment before therapeutic benefit is felt. Unwanted side effects, related to all classes of anti-depressant drugs, can be intolerable and in some patients depressive symptoms may actually become more severe with treatment. Many pharmacological agents are available for the treatment of depression however these are not without their limitations in both efficacy and tolerability.

Three major problems are commonly associated with typical anti-depressant treatments. First there is a large population of patients that do not respond to conventional drug therapy (Stahl et al., 2001). Second, patients experience a long latency period before gaining any therapeutic benefit (Gumnick et al). Lastly, most anti-depressants have a wide range of unwanted side-effects that are related to modulation of brain neurotransmitters and their specific receptors subtypes (Ereshefsky et al., 1997).

Therefore, there exists a need for improved treatments for psychotic disorders that are safe, efficacious and have limited side-effects.

SUMMARY OF THE INVENTION

According to a first aspect, the present invention is directed to an isolated cell obtainable from the CTX0E03 neural stem cell line for use in the treatment of a disorder associated with elevated levels of pro-inflammatory cytokines, particularly a disorder selected from unipolar and bipolar depression, schizophrenia, obsessive compulsive disorder, autism and autistic syndrome disorders.

According to a second aspect, the present invention provides a method for determining the potential effectiveness of cells of the CTX0E03 stem cell line for use as a therapy in the treatment of a psychiatric disorder, comprising the steps of: contacting a sample of peripheral blood cells from a patient suffering from a psychiatric disorder with cells of the cell line; and determining the effect of the cells on the pro-inflammatory cytokine response of the peripheral blood cells. In a preferred embodiment, the psychiatric disorder is selected from unipolar and bipolar depression, schizophrenia, obsessive compulsive disorder, autism and autistic syndrome disorders.

DESCRIPTION OF THE DRAWINGS

FIGS. 2A(ii)-2A(v) are representative low (ii, iii) and high (iv, v) fluorescent images showing GFAP expression in HTS, vehicle-treated (ii, iv) and CTX0E03-treated (iii, v) brains;

FIGS. 2B(ii)-2B(iii) are representative fluorescent images showing TGF-β positive microglia (ii) and microglia stained with haematoxylin and eosin (iii);

FIGS. 4A and 4B are graphs showing the dose-dependent effect of differentiated CTX0E03 on the reduction of LPS-stimulated PBMC IFN-γ in vitro (p=<0.01);

FIG. 5 is a graph showing the dose-dependent effect of IFN-γ on CTX0E03-mediated production of IDO;

DETAILED DESCRIPTION OF THE INVENTION

Figure 1:
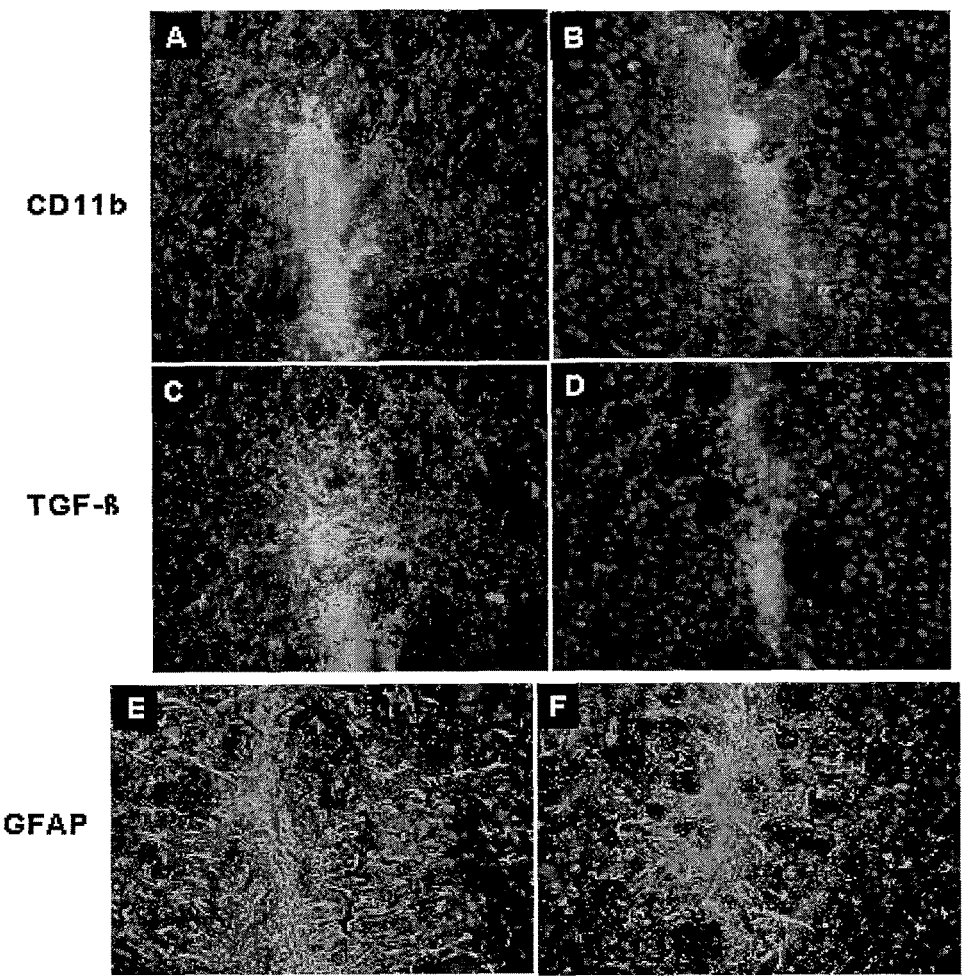
FIG. 1 shows fluorescent images of microglial and astrocytic responses in the mouse brain at 7 days post vehicle (1A, 1C, 1E) and 7 days post CTX0E03 treatment (1B, 1D, 1F)

The present invention is based on the surprising discovery that cells of the CTX0E03 cell line, are able to reduce, modulate or inhibit pro-inflammatory cytokines in vivo, and are therefore able to modulate or inhibit activation of T cells and other cells of the immune system. As such, these cells are useful in the treatment of disorders associated with elevated levels of pro-inflammatory cytokines, compared with a control, and disorders characterised by elevated levels of one or more inflammatory marker, compared with a control. These cells provide an industrially scalable, safe and potent allogeneic treatment.

In particular, the present invention is directed to the use of cells obtained from the CTX0E03 cell line in the treatment of psychiatric disorders, including unipolar and bipolar depression, stress-induced depression, obsessive compulsive disorder, bipolar disorder, schizophrenia and autism or autistic syndrome disorders.

The cells of the CTX0E0E cell line have the following characteristics:

Multipotent cells.
Derived from a single founder cell (clonal cells).
Genetically stable cells with normal chromosomes.
Can be grown in large numbers and stored.
Are safe, particularly not showing tumourigenic potential.
Migration, once implanted, is limited to areas of tissue damage.
Are efficacious in recognised animal models.
Provenance is fully documented.

In a preferred embodiment, the present invention relates to the treatment of depressed patients with depressive symptoms that do not respond to common anti-depressant medication.

As used herein, the term "pro-inflammatory cytokine" has its usual meaning in the art and refers to a cytokine which promotes systemic inflammation. Examples of pro-inflammatory cytokines include interleukin-1 (IL-1), tumour necrosis factor-alpha (TNF-α), necrosis factor-beta (TNF-β) and interferon-gamma (IFN-γ).

The neural stem cell line CTX0E03 has been deposited at the European Collection of Animal Cultures (ECACC), Vaccine Research and Production laboratories, Public Health Laboratory Services, Porton Down, Salisbury, Wiltshire, SP4 0JG, UK. The ECACC Accession No. is 04091601. The derivation of this cell line is described in European Patent No. 1645626 the content of which is incorporated herein by reference.

The cells of the CTX0E03 cell line may be cultured in the following culture conditions:

| | |
|---|---|
| Human Serum Albumin | 0.03% |
| Transferrin, Human | 100 μg/ml |
| Putrescine Dihydrochloride | 16.2 μg/ml |
| Insulin Human recombinant | 5 μg/ml |
| Progesterone | 60 ng/ml |
| L-Glutamine | 2 mM |
| Sodium Selenite (selenium) | 40 ng/ml |

Plus basic Fiboblast Growth Factor (10 ng/ml), epidermal growth factor (20 ng/ml) and 4-hydroxytamoxifen 100 nM for cell expansion. The cells can be differentiated by removal of the 4-hydroxytamoxifen, which will occur on administration of the cells to the patient.

The development of the CTX0E03 cell line has allowed the scale-up of a consistent product for clinical use. Production of cells from banked materials allows for the generation of cells in quantities for commercial application.

As used herein, the term "psychiatric disorder" refers to chronic behavioural disorders typically involving systemic and brain inflammation. Disorders include unipolar and bipolar depression, schizophrenia, obsessive compulsive disorder, autism and autistic syndrome disorders.

As used herein, the term 'patient' refers to a mammal including a non-primate (e.g. a cow, pig, horse, dog, cat, rat and mouse) and primate (e.g. a monkey and human), and more preferably a human.

Methods for the preparation of formulations for delivery to a patient will be apparent to the skilled person. Suitable excipients, diluents etc., will again be apparent based on current practice in preparing neural stem cell-based therapies and described in the literature. The amount of cells required for delivery will vary depending on the form of treatment, the severity of the disease, and the need for applying multiple doses over a treatment period. However, the skilled person can readily determine the appropriate treatment based on existing cell transplantation therapies.

Suitable routes of administration of cells according to the invention include direct intra-venous, intra-arterial, intra-muscular or intra-cerebral injection. The cells will be administered preferably in the undifferentiated state.

In a preferred embodiment, the cells for transplantation are suspended in a composition comprising Trolox, $Na^+$, $K^+$, $Ca^{2+}$, $mg^{2+}$, $Cl^-$, $H_2PO_4^-$, HEPES, lactobionate, sucrose, mannitol, glucose, dextron-40, adenosine and glutathione. Preferably, the composition will not include a dipolar aprotic solvent, e.g. DMSO. Suitable compositions are available commercially, e.g. HypoThermasol®-FRS. Such compositions are preferred as they allow the cells to be stored at 4° C. to 25° C. for extended periods (hours to days) or preserved at cryothermic temperatures, i.e. temperatures below −20° C. The cells may then be administered in this composition after thawing.

In a further embodiment, the present invention is directed to a method for determining the potential effectiveness of the cells the CTX0E03 cell line for use as a therapy in the treatment of a psychiatric disorder, said method comprising the steps of: contacting a sample of peripheral blood cells from a patient suffering from a psychiatric disorder with cells of the cell line; and determining the effect of the cells of the cell line on the pro-inflammatory cytokine response of the peripheral blood cells. In a preferred embodiment, the psychiatric disorder is selected from unipolar and bipolar depression, schizophrenia, obsessive compulsive disorder, autism and autistic syndrome disorders. If the cells reduce or modulate pro-inflammatory cytokines, this indicates a potential for use in treating said disorders.

It is proposed that the mechanism by which CTX0E03 cells inhibit or modulate pro-inflammatory cytokines, and thereby inhibit or reduce inflammation, including microglial and T cell activation, involves the cell-surface expression of the programmed cell death ligand CD274. Up-regulation of CD274 requires IFN-γ which, as shown in the data described above, results in abrogation of PBMC IFN-γ production. Therefore, it appears that the immunosuppressive activity of CTX0E03 cells is driven by the presence of pro-inflammatory cytokines (such as IFN-γ) and the immuno-modulatory activity of CTX0E03 cells following implantation in vivo is mediated in part by CD274 upregulation which is triggered by the inflammatory microenvironment surrounding the cells.

The invention will now be described with reference to the following non-limiting examples:

EXAMPLE 1

CTX0E03 Cells Reduce Host Astrocyte and Microglia Responses in the Mouse Brain

Adult male BalbC mice were implanted with CTX0E03 cells or control vehicles in the striatal region of the brain. 7 days post grafting brains were collected and subjected to histological analysis. Fluorescence immunohistochemistry, using specific markers to detect astrocytes (Glial fibrillary acid protein, GFAP) and microglia (CD11 b, TGF-β) was performed.

The results are presented in FIGS. 1A-F. As can be seen, CTX0E03 treatment afforded a reduction in GFAP, CD11 b and TGF-β expression in the striatum, at the site of implantation, compared with vehicle control-treated brains.

EXAMPLE 2

CTX0E03 Cells Reduce Host Astrocyte and Microglia Responses in the Mouse Brain

Adult male BalbC mice were implanted with CTX0E03 cells, or control vehicles in the striatal region of the brain. At 4, 24, 48, 72 hours and 7 days post-implantation, brains were collected and subjected to histological analysis. Fluorescence immunohistochemistry, using specific markers to detect astrocytes (GFAP) and microglia (TGF-β) was performed. Host astrocytes and microglia responses were quantified by measuring GFAP and TGF-β fluorescent signals by image analysis.

Figure 2:
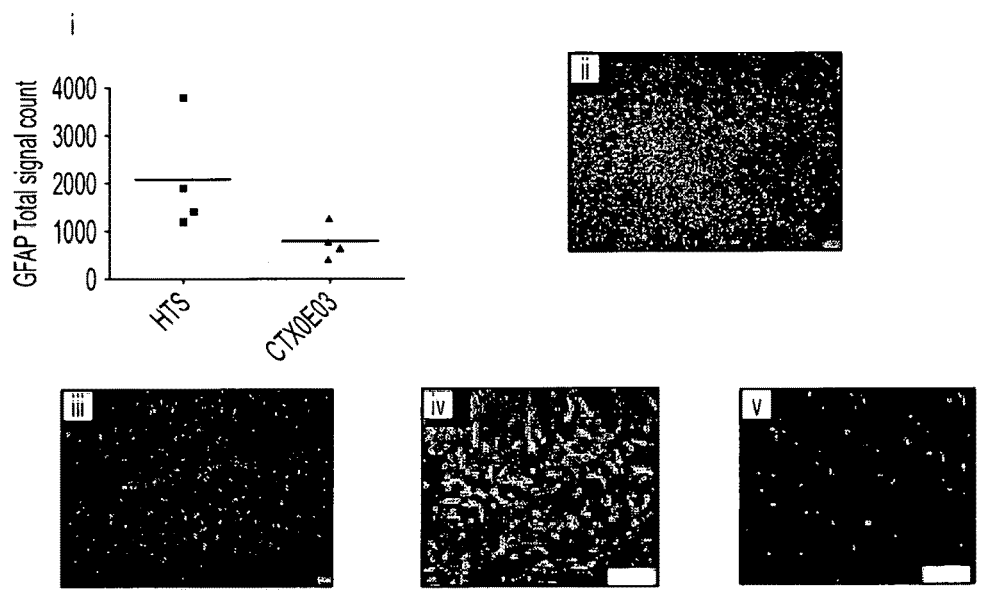
FIG. 2A(i) is a graph showing a reduction in total GFAP fluorescent signal with CTX0E03-treated mouse brains compared with HTS vehicle-treated mouse brains.
FIG. 2B(i) is a graph showing a significant reduction in TGF-β fluorescent signal with CTX0E03-treated mouse brains compared with HTS vehicle-treated mouse brains.
Figure 2:
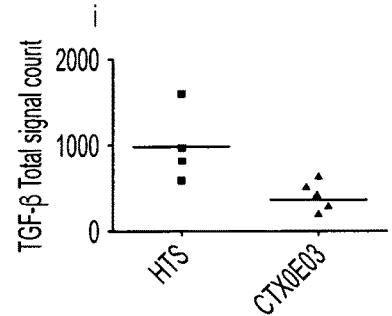
Figure 2:

The GFAP host responses are illustrated in FIG. 2A. CTX0E03 treatment reduced GFAP host responses at 72 hours post-implantation, compared with vehicle-treated brains. The reactive morphology demonstrated by vehicle treated brains at this time point was not observed in CTX0E03-treated brains.

The microglial host responses are illustrated in FIG. 2B. CTX0E03 treatment significantly reduced TGF-β host responses at 72 hours post implantation compared with vehicle-treated brains.

EXAMPLE 3

CTX0E03 Cells Significantly Reduce the Production of IFN-γ when Cultured with Lipopolysaccharide (LPS)—Stimulated Mixed Human Peripheral Blood Mononuclear Cells (PBMCs) Compared with Control PBMCs Mitomycin treated (growth arrested) or differentiated (growth factors removed) CTX0E03 cells were cultured in 96 well plates with LPS stimulated human PBMCs for 24 hours at 37° C. After 24 hours, culture plates were centrifuged at 1500 rpm and the cell supernatants analysed for interferon-gamma (IFN gamma) by ELISA.

Figure 3A:
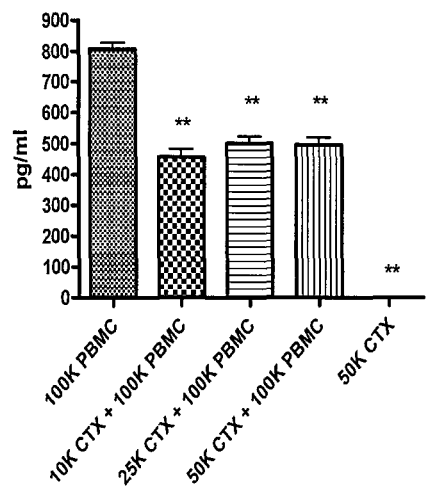
FIGS. 3A and 3B are graphs showing the significant effect of mitomycin-treated CTX0E03 on the reduction of LPS-stimulated PBMC IFN-γ in vitro (p=<0.01)
Figure 3B:
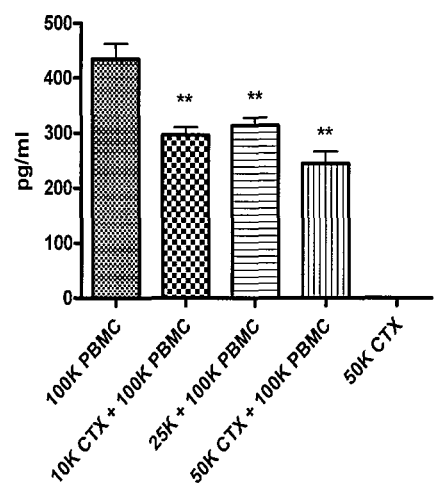

Mitomycin treated CTX0E03 cells significantly reduced PBMC IFN-γ production, but there was no dose-dependent effect; these results are shown in FIG. 3.

Differentiated CTX0E03 demonstrated a significant and dose-dependent reduction of PBMC IFN-γ production, with complete abrogation of the response as demonstrated with CTX0E03 at 25K and 50K (see FIG. 4).

EXAMPLE 4

Microarray and Quantitative Polymerase Chain Reaction (QPCR) Demonstrate Significant Up-Regulation of Indoleamine 2,3-Dioxygenase (IDO) and Programmed Death Ligand-1 (PDL-1) in Response to IFN-γ

Microarray analysis of genes associated with inflammation was performed on CTX0E03 cells stimulated with IFN-γ using the OpenArray™ system. Expression of 359 genes was detected, including up-regulation of CD274 (Progammed Death Ligand-1 (PDL-1)).

Table 1 shows the CTX0E03 inflammation genes significantly up- or down-regulated by IFN-γ treatment.

Real-time PCR analysis of CTX0E03 mediated Indoleamine 2, 3 dioxygenase (IDO) production was also performed following treatment with IFN γ and a dose-response effect of IFN-γ on CTX0E03-mediated production of IDO was demonstrated (see FIG. 5).

TABLE 1

| | AVG ΔC_t | | 2^−ΔC_t | | Fold up- or down- regulation | | |
|---|---|---|---|---|---|---|---|
| | Group 1 | Control group | Group 1 | Control group | Group 1/control | Biotrove | Biotrove |
| CD74 #50 | −0.32 | 8.9 | 1.248331 | 0.002101 | 594.28 | CD74 | 630.44 |
| CD74 #57 | 1.21 | 10.42 | 0.430773 | 0.00073 | 590.18 | | |
| IL 18BP #59 | 0.53 | 9.38 | 0.694959 | 0.001501 | 463.04 | IL 18BP | 128.37 |
| IL 18BP #61 | −0.2 | 8.49 | 1.144724 | 0.002781 | 411.57 | | |
| CD274 #25 | 2.98 | 10.56 | 0.126306 | 0.000665 | 190.02 | CD274 | 64.14 |
| CD274 #88 | 3.81 | 11.68 | 0.071545 | 0.000306 | 233.94 | | |
| CSF1 #2 | 2.54 | 8 | 0.171943 | 0.00392 | 43.87 | CSF1 | 32.72 |
| CSF1 #19 | 2.41 | 7.76 | 0.188809 | 0.004613 | 40.93 | | |
| IL 15 #46 | 6.97 | 12.84 | 0.008004 | 0.000136 | 58.69 | IL15 | 19.92 |
| SOCS #87 | 4.01 | 10.38 | 0.062068 | 0.000753 | 82.42 | SOCS1 | 23.71 |
| SOCS #12 | 7.27 | 10.98 | 0.006502 | 0.000495 | 13.13 | | |
| PTX3 #58 | 10.01 | 11.42 | 0.00097 | 0.000366 | 2.65 | PTX3 | 6.05 |

EXAMPLE 5

Blocking Studies Demonstrate that Abrogation of PBMC IFN-γ by CTX0E03 is PDL-1 Mediated Differentiated (growth factors removed) CTX0E03 cells were cultured in 96 well plates with LPS stimulated human PBMCs for 24 hours at 37° C. with the addition of an anti-CD274 (PDL-1) functional blocking antibody. After 24 hours, culture plates were centrifuged at 1500 rpm and the cell supernatants analysed for interferon-gamma (IFN gamma) by ELISA.

Figure 6:
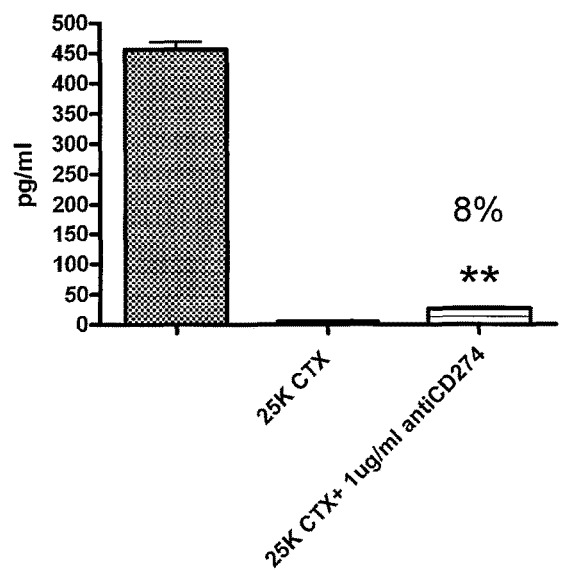
FIG. 6 is a graph showing the effect of anti-CD274 blocking antibody on CTX0E03-induced immunosuppression (p=<0.01)

Treatment with the anti-CD274 (PDL-1) functional blocking antibody significantly reversed the CTX0E03 abrogation of PBMC IFN-γ production, as shown in FIG. 6.

EXAMPLE 6

CTX0E03 Cells Express IDO and PDL-1 Following Intra-Cerebral Implantation

Cell smears of CTX0E03 drug product were produced on glass microscope slides and were subjected fluorescence immunohistochemistry, using specific markers to detect IDO and CD274 (PDL-1).

Adult male BalbC mice were implanted with CTX0E03 cells in the striatal region of the brain. At 4, 24, 48, 72 hours and 7 days post grafting, brains were collected and subjected fluorescence immunohistochemistry, using specific markers to detect IDO and CD274 (PDL-1).

Figure 7:
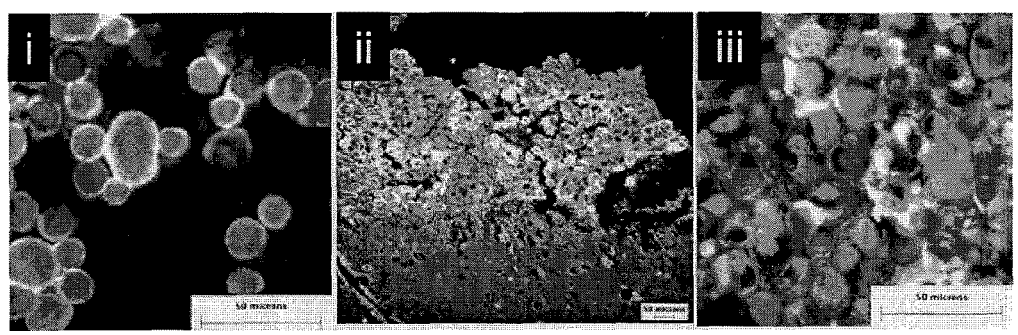
FIG. 7 shows images of (i) high expression of IDO by CTX0E03 drug product prior to implantation, and (ii & iii) up-regulation of IDO expression by CTX0E03 cells 24 hours post implantation.

Cytoplasmic expression of IDO was demonstrated in approximately 95% of CTX0E03 cells prior to in vivo implantation. Up to 24 hours post intra-cerebral implantation 100% of surviving CTX0E03 cells expressed IDO. The expression of IDO was lost in surviving cells at later time points post implantation, see FIG. 7.

Figure 8:
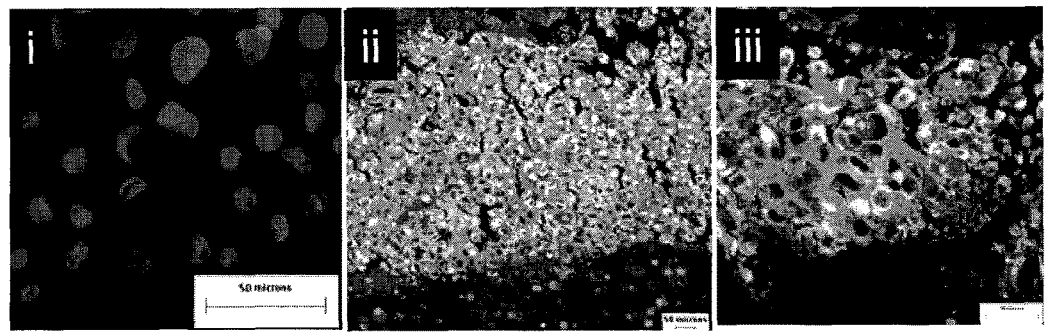
FIG. 8 shows images of (i) no expression of CD274 (PDL-1) by CTX0E03 drug product prior to implantation and (ii & iii) up-regulation and sustained expression of CD274 (PDL-1) by CTX0E03 up to 7 days post implantation.
Figure 9A:
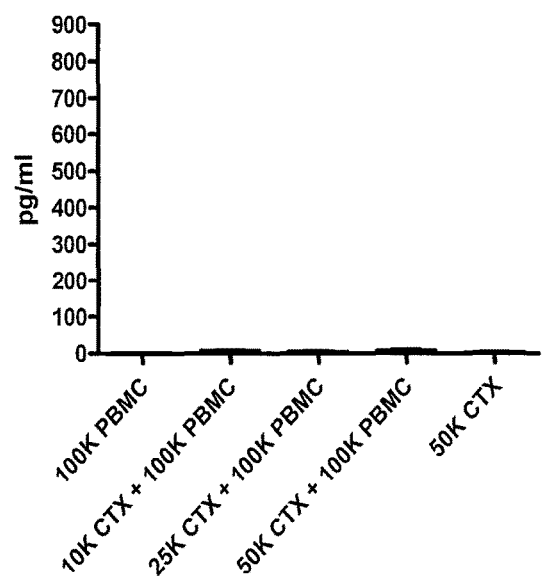
FIG. 9 (A-E) are graphs showing that CTX0E03 cells inhibit the LPS release of IFN-γ from human PBMCs in a concentration-dependent manner.
Figure 9B:
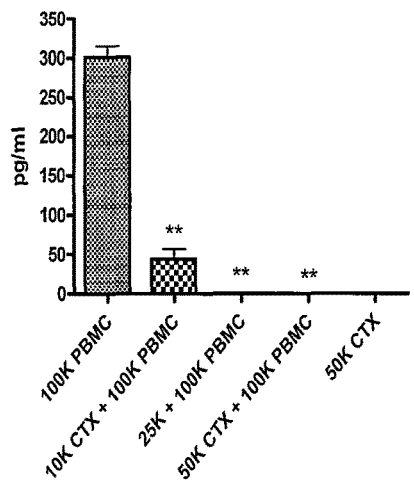
Figure 9C:
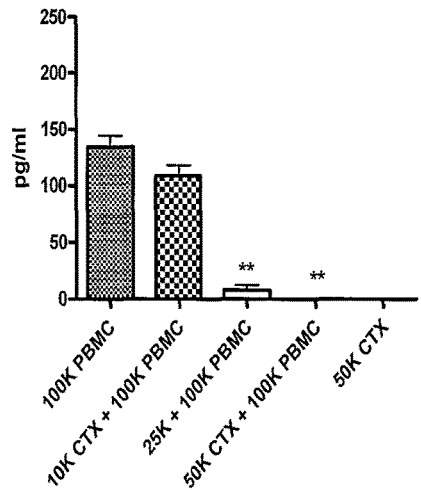
Figure 9D:
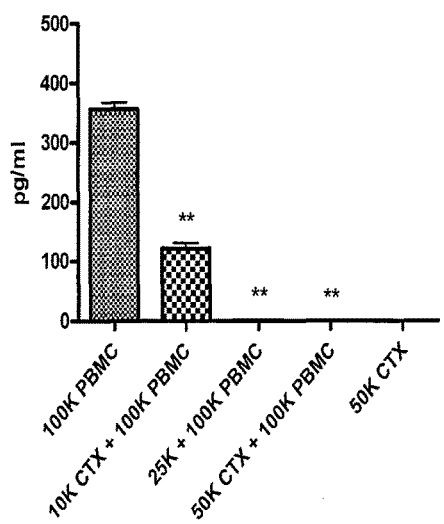
Figure 9E:
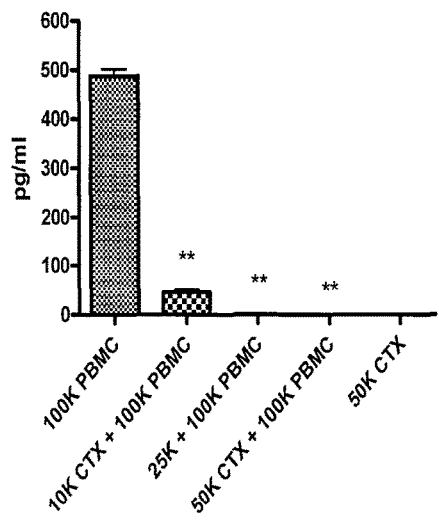

CTX0E03 did not demonstrate CD274 (PDL-1) expression prior to implantation. A significant up-regulation of this protein was observed in CTX0E03 cells post intracerebral implantation. Cytoplasmic expression of this protein was present on CTX0E03 cells up to 7 days post implantation and appeared to be more prominent in CTX0E03 with mature neuronal like morphology at the later time points, see FIG. 8.

EXAMPLE 7

Involvement of CD274 in CTX0E03 Mediated Suppression of T Cell Activation

Lymphocyte reactions were performed with 7 day growth-arrested CTX0E03 cells combined with 100,000 human peripheral blood mononuclear cells (PBMC) per well of a 96 well plate for 24 hours. Where stated, LPS was added at 50 ng/ml. Functional experiments using a blocking antibody (eBioscience) was added to CTX0E03 cells 2 hours prior to PBMCs (10 μg/ml).

FIG. 9 (A-E) shows that CTX0E03 cells inhibit the LPS release of IFN-γ from human PBMCs, isolated from a variety of donors. The IFN-γ levels within a co-culture of CTX0E03 cells with unstimulated (no LPS) human PBMCs are shown in FIG. 9A. FIGS. 9B-E demonstrate IFN-γ levels within a co-culture of LPS stimulated human PBMCs and CTX0E03 cells from different donors (p<0.01). These data show that CTX0E03 cells inhibit IFN-γ release in a concentration-dependent manner.

Figure 10A:
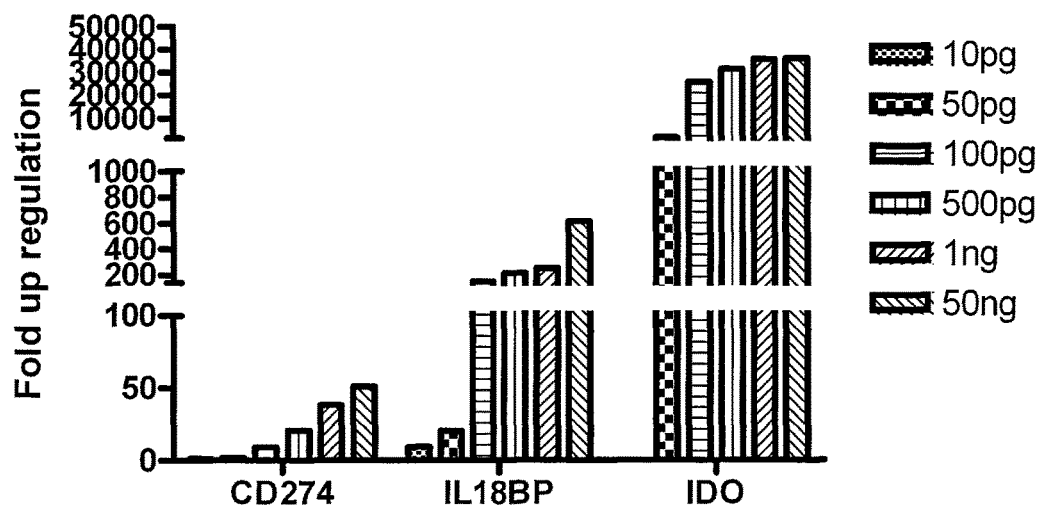
FIG. 10 (A-B) illustrates the expression profiling of CTX0E03 cells.
FIG. 10B is a graph showing that pre-incubation of CTX0E03 cells with a blocking antibody raised against human CD274 (10 μg/ml for 2 hours) prior to co-culture with LPS stimulates PBMCs and restores the inhibition induced by CTX0E03 cells.
Figure 10B:
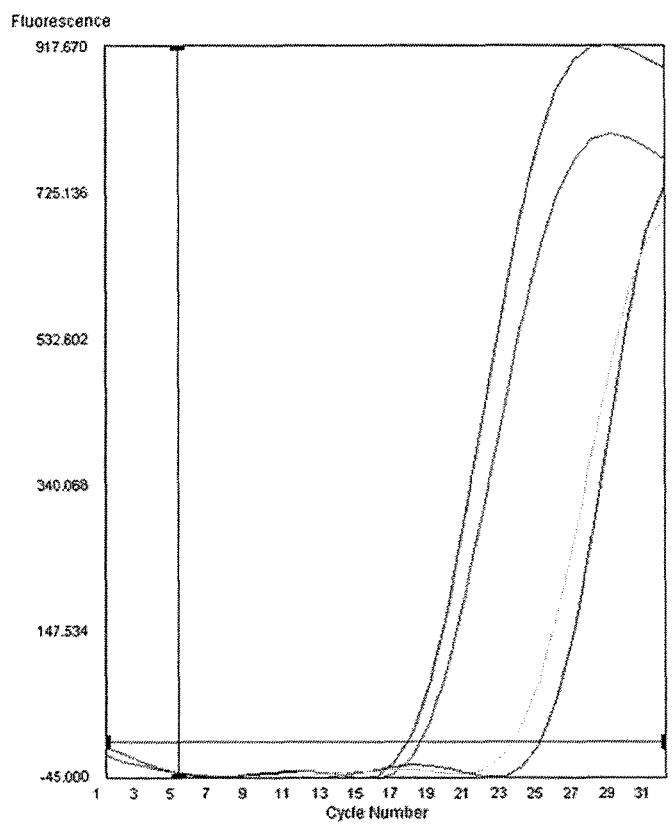

FIG. 10 (A and B) illustrates the expression profiling of CTX0E03 cells. Real-time PCR illustrates the relative expression levels of known immune modulators in the presence of absence (control) of IFN-γ. As shown in FIG. 10A, the expression level of each gene was dependent upon the concentration of IFN-γ. As Table 2, IFN-γ had no effect on the expression level of certain genes, even at 50 ng/ml. A fold increase greater than 4 was considered significant.

TABLE 2

| | AVG ΔC, | | 2^-ΔC, | | Fold Up Regulation |
| --- | --- | --- | --- | --- | --- |
| | 50 ng/ml IFNγ | Control | 50 ng/ml IFNγ | Control | 50 ng/ml IFNγ/Control |
| IDO | −1.69 | 14.08 | 3.226567 | 0.000058 | 55878.28 |
| IL18BP | 1.062 | 7.64 | 3.063116 | 0.005031 | 608.87 |
| CD274 | 3.48 | 9.15 | 0.089933 | 0.001766 | 50.91 |
| TRL4 | 4.81 | 5.92 | 0.035649 | 0.016459 | 2.17 |

Figure 11A:
FIG. 11A is an image showing that the addition of the pro-inflammatory cytokine IFN-γ in vitro induces CTX0E03 cells to express CD274.
Figure 11B:
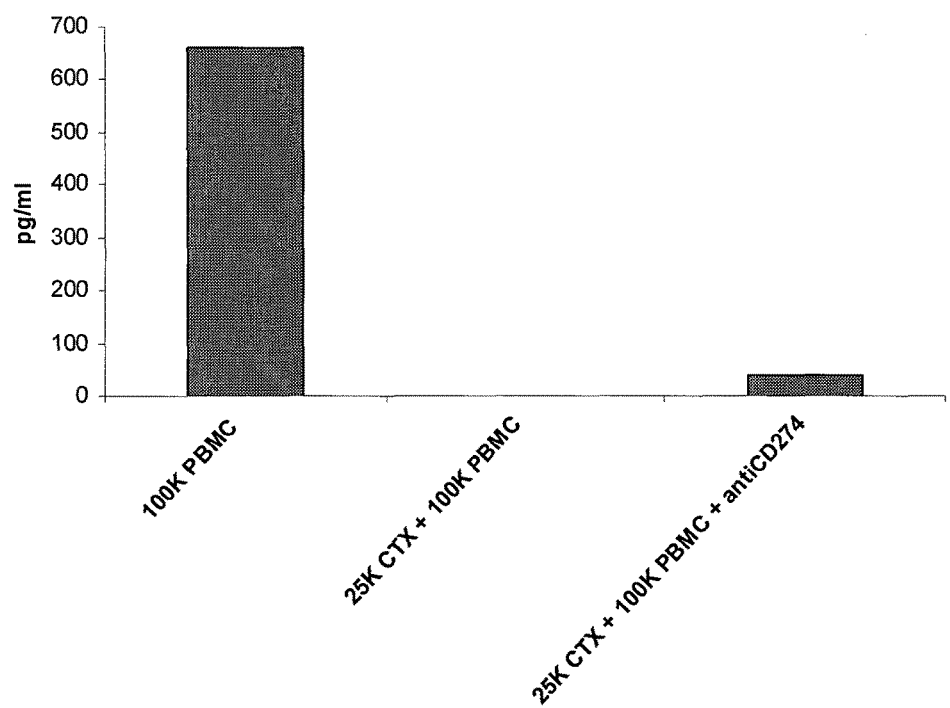
FIG. 11C shows the proposed mechanism of action illustrating the requirement of an inflammatory environment to activate the cells' immunosuppressive function.
Figure 11C:
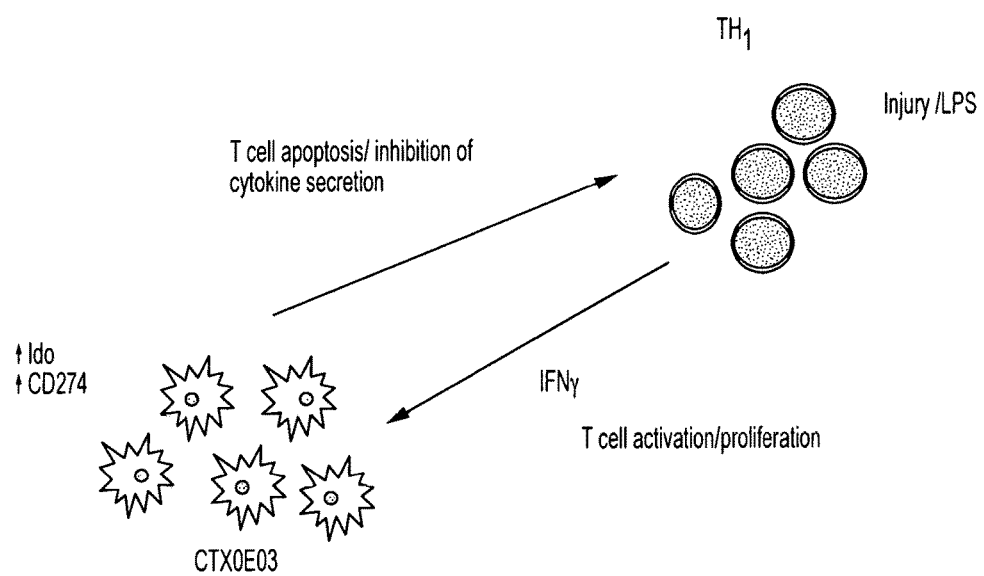

FIG. 11A shows that the addition of the pro-inflammatory cytokine IFN-γ in vitro induced CTX0E03 cells to express CD274. Pre-incubation of CTX0E03 cells with a blocking antibody raised against human CD274 (10 µg/ml for 2 hours) prior to co-culture with LPS stimulated PBMCs (n=3) and restored an average of 8.3% of the inhibition induced by CTX0E03 cells. This is shown in FIG. 11B. FIG. 11C shows the proposed mechanism of action illustrating the requirement of an inflammatory environment to activate the cells' immunosuppressive function.

REFERENCES

1. Lopez A D, Murray C C (1998) The Global Burden of disease, 1990-2020. Nat Med 4(11):1241-3.
2. Gumnick J F, Nemeroff C B (2000) Problems with currently available antidepressants. J Clin Psychiatry 61(10):5-15.
3. Wong M L, Licinio J (2001) Research and treatment approaches to depression. Nature Reviews Neuroscience 2: 343-351.
4. Caspi A, Sugden K, Moffitt T E, Taylor A, Craig I W, Harrington H, McClay J, Mill J, Martin J, Braithwaite A, Poulton R (2003) Influence of life stress on depression: Moderation by a polymorphism in the 5-HTT gene. Science 301:386-389.
5. Heuser I (1998) The hypothalamic-pituitary-adrenal system in depression. Pharmacopsychiatry 31:10-13.
6. Young E A, Haskett R F, Murphy-Weinburg V, Watson S J, Akil H (1991) Loss of glucocorticoid fast feedback in depression. Arch Gen Psychiatry 48: 693-699.
7. Sheline Y I, Wany P, Gado M H, Csernansky J G, Vannier M W (1996) Hippocampal atrophy in recurrent major depression. Proc Natl Acad Sci USA 93:3908-3913.
8. Sapolsky R M (1996) Glucocorticoids and atrophy of the human hippocampus. Science 273:749-775.
9. Bremner J D, Randall P, Scott T M, Bronen R A, Seibyl J P, Southwick S M, Delaney R C, McCarthy G, Charney D S, Innis R B (1995) MRI-based measurement of hippocampal volume in patients with combat related post-traumatic stress disorder.
10. Watanabe Y, Gould E, McEwen B S (1982) Stress induces atrophy of apical dendrites of hippocampal CA3 pyramidal neurones. Brain Res 588:341-345.
11. Sapolsky R M, Krey L C, McEwen B S (1985) Prolonged glucocorticoid exposure reduces hippocampal neurone number: implications for aging. J Neurosci 5:1222-1227.
12. Uno H, Tarara R, Else J G, Suleman M A, Sapolsky R M (1998) Hippocampal damage associated with prolonged and fatal death in primates. J Neurosci 9:1705-1711.
13. Sapolsky R M (1990) Glucocorticoids, hippocampus, and the glutamatergic synapse. Frog Brain Res 86:13-23.
14. Wooley C S, Gould E, McEwen B S (1990) Exposure to excess glucocorticoids alters dendritic morphology of adult hippocampal pyramidal neurones. Brain Res 531: 225-231.
15. Stein-Beherens B, Mattson M P, Chang I, Yeh M, Sapolsky R (1994) Stress exacerbates neurone loss and cytoskeletal pathology in the hippocampus. J Neurosci 14:5373-5380.
16. Margarinos A M, McEwen B S, Flugge G, Fuchs E (1996) Chronic psychosocial stress causes apical dendritic atrophy of hippocampal CA3 pyramidal neurones in subordinate tree shrews. J Neurosci 16:3534-3540.
17. Elkis H, Friedman L, Wise A, Meltzer H Y (1995) Meta-analysis of studies of ventricular enlargement and cortical sulcal prominence in mood disorders. Arch Gen Psychiatry 52:735-746.
18. Schiepers O J, Wichers M C, Maes M (2005) Cytokines and major depression. Prog Neuropsycopharmacol Biol Psychiatry 29(2):201-217.
19. Dunn A J, Swiergiel A H, de Beaurepaire R (2005) Cytokines as mediators of depression: what can we learn from animal studies Neurosci Biobeh Rev 29:891-909.
20. Kim Y K, Na K S, Shin K H, Jung H Y, Choi S H, Kim J B (2007) Cytokine imbalance in the pathophysiology of major depressive disorder. Prog Neuropsycopharmacol Biol Psychiatry 31(5):1044-1053.
21. Brambilla F, Monteleone P, Maj M (2004) Interleukin-1beta and tumor necrosis factor alpha in children with major depressive disorder or dysthymia. J Affect Disord 78:273-277.
22. Konuk N, Tekin I O, Ozturk U, Atik L, Atasoy N, Bektas S, Erdogan A (2007) Plasma levels of tumor necrosis factor-alpha and Interleukin-6 in obsessive compulsive disorder. Mediators Inflamm 2007:65704.
23. Goshen I, Yirmiya R (2009) Interleukin-1 (IL-1): A central regulator of stress responses. Front Neuroendocrinol 30:30-45.
24. Koo J W, Duman R S (2008) IL-1beta is an essential mediator of the antineurogenic and anhedonic effects of stress. Proc Natl Acad Sci USA 105(2):751-6.
25. Ben Menachem-Zidon O, Goshen I, Kriesle T, Ben Menachem Y, Reinhartz E, Ben Hur T, Yirmiya R (2008) Intrahippocampal transplantation of transgenic Neural precursor cells overexpressing Interleukin 1 receptor antagonist blocks chronic isolation induced impairment in memory and neurogenesis. Neuropsychopharmacol 33:2251-2262.
26. Sluzewska A, Rybakowski J, Bosmans E, Sobieska M, Berghmans R, Maes M, Wiktorowicz K (1996) Indicators of immune activation in major depressive illness. Psychiatry Res 64:161-167.
27. Basterzi A D, Aydemir C, Kisa C, Aksaray S, Tuzer V, Yazici K, GOka E (2005) IL-6 levels decrease with SSRI treatment in patients with major depression. Hum Psycopharmacol 20:473-476.
28. Malberg J E, Eisch A J, Nestler E J, Duman R S (2000) Chronic antidepressant treatment increases neurogenesis in the adult rat hippocampus. J Neurosci 20(24):9104-9110.

29. Malberg J E, Duman R S (2003) Cell proliferation in the adult hippocampus is decreased by inescapable stress: Reversal by Fluoxetine treatment. Neuropsychopharmacology 28:1562-1571.
30. Sahay A, Hen R (2007) Adult hippocampal neurogenesis in depression. Nat Neurosci 1%9):1110-1115.
31. Santarelli L, Saxe M, Gross C, Surge T A, Battaglia F, Dulawa S, Weisstaub N, Lee J, Duman R, Arancio O, Belzung C, Hen R (2003) Requirement of hippocampul neurogenesis for the behavioural effects of antidepressants. Science 3012:805-809.
32. O'Brien S, Scully P, Fitzgerald P, Scott L V, Dinan T G (2007) Plasma cytokine profiles in depressed patients who fail to respond to selective serotonin reuptake inhibitor therapy. J Psychiatr Res 2007; 41:326-331.
33. Eller T, Vasar V, Shlik J, Maron E (2008) Proinflammatory cytokines and treatment response to escitalopram in major depressive disorder. Frog Neuropsychopharmacol Biol Psychiatry 2008; 32:445-450.
34. Hong Z F, Huang X J, Yin Z Y, Zhao W X, Wang X M (2009) Immunosuppressive function of bone marrow mesenchymal stem cells on acute rejection of liver allografts in rats. Transplantation Proceedings 41:403-409.
35. Li Y, Tredget E E, Ghaffari A, Lin X, Kilani R T, Ghahary A (2006) Local expression of indoleamine 2,3-dioxygenase protects engraftment of xenogeneic substitute. Journal Invest Dermatol 126:128-136.
36. Stroemer P, Patel S, Hope A, Oliveira C, Pollock K, Sinden J (2009) The neural stem cell line CTX0E03 promotes behavioural recovery and endogenous neurogenesis after experimental stroke in a dose dependent fashion. Neurorehabil Neural Repair 23(9):895-909.
37. Park D H, Eve D J, Sanberg P R, Musso J 3rd, Bachstetter A D, Wolfson A, Schlunk A, Baradez M O, Sinden J D, Gemma C (2010) Increased neuronal proliferation in the dentate gyrus of aged rats following neural stem cell implantation. Stem Cells Dev 19(2):175-180.
38. Couillard-Depres S, Wuertinger C, Kandasamy M, Caioni M, Stadler K, Aigner R, Bogdahn U, Aigner L (2009) Ageing abolishes the effects of fluoxetine on neurogenesis. Mol Psychiatry 14(9):856-864.
39. Tfilin M, Sudai E, Merenlender A, Gispan I, Yadid G, Turgeman (2009) Mesenchymal stem cells increase hippocampal neurogenesis and counteract depressive-like behaviour. Molecular Psychiatry 1-12.
40. Stahl S M, Nierenburg A A, Gorman J M (2001) Evidence of early onset of antidepressant effect in randomized controlled trials. J Clin Psychiatry 62 (4):17-23.
41. Ereshefsky L, Alfaro C L, Lam Y W F (1997) Treating depression: potential drug interactions. Psych Ann 27:244-258.
42. Fink F (2001) Convulsive therapy: a review of the first 55 years. J Affect Disord 63 (1-3):1-15.
43. Zetterstrom T S C, Pei Q, Grahame-Smith D G (1998) Repeated electric convulsive shock extends the duration of enhanced expression of BDNF in rat brain compared with a single administration. Mol Brain Res 57:106-110.
44. Skolnick P, Legutko B, Li X, Bymaster F P (2001) Current perspectives on the development of non-biogenic amine-based antidepressants. Pharmacological Research 43 (5):411-422.
45. Himmelhoch J M (1995) Monoamine oxidase inhibitors. Kaplan H I, Sadock B J, eds. Comprehensive Textbook of Psychiatry. $6^{th}$ ed. Baltimore, Md.: Williams and Wilkins 2038-2054.
46. Janicak P G, Davis J M, Preskorn S H (1997) Principles and practice of clinical psycopharmacotherapy $2^{nd}$ ed. Baltimore, Md.: Williams and Wilkins.

The invention claimed is:
1. A method for treating a patient having unipolar or bipolar depression, wherein said method comprises administering to the patient a composition comprising a cell obtainable from the CTX0E03 neural stem cell line.
2. The method according to claim 1, wherein the cell is administered by direct intra-cerebral, intra-ventricular or systemic implantation.
3. A method for treating a patient having unipolar or bipolar depression, wherein said method comprises administering to the patient a composition comprising a cell obtainable from the CTX0E03 neural stem cell line, wherein the patient has an elevated level, systemically or in the brain, of one or more pro-inflammatory cytokines at the time of said administering, and wherein the cell expresses Programmed Death Ligand-1 (PDL-1) in the patient.

* * * * *